(12) United States Patent
Keller

(10) Patent No.: US 8,398,562 B2
(45) Date of Patent: Mar. 19, 2013

(54) EAR CANAL PRESSURIZATION DEVICE

(75) Inventor: James E. Keller, Murphy, NC (US)

(73) Assignee: Micro Audiometrics Corporation, Murphy, NC (US)

( * ) Notice: Subject to any disclaimer, the term of this patent is extended or adjusted under 35 U.S.C. 154(b) by 1411 days.

(21) Appl. No.: 11/772,263

(22) Filed: Jul. 2, 2007

(65) Prior Publication Data

US 2009/0012420 A1 Jan. 8, 2009

(51) Int. Cl.
*A61B 5/00* (2006.01)
*A61B 5/12* (2006.01)
*A61F 11/00* (2006.01)
*A61F 11/06* (2006.01)
*A61H 1/00* (2006.01)

(52) U.S. Cl. .......... 600/559; 73/585; 128/864; 128/867; 128/868; 601/76; 601/77

(58) Field of Classification Search .................. 600/559; 73/585; 128/864, 867, 868; 601/76, 77
See application file for complete search history.

(56) References Cited

U.S. PATENT DOCUMENTS

| 6,159,171 | A * | 12/2000 | Densert et al. ................ 601/76 |
| 6,629,938 | B1 * | 10/2003 | Engvall et al. ................ 601/76 |
| 2006/0197412 | A1 | 9/2006 | Rasmussen | |

* cited by examiner

*Primary Examiner* — Sean P Dougherty
*Assistant Examiner* — Devin Henson
(74) *Attorney, Agent, or Firm* — Luedeka Neely Group, P.C.

(57) ABSTRACT

An ear canal pressurization device optimized for aural acoustic immittance testing is disclosed. Changes in volume of a first flexible chamber, due to motor movement, produce changes in ear canal pressure based on Boyle's law. A vent may be opened to allow ear canal pressure to gently equalize to ambient air pressure or to generate ear canal pressure sweeps free of pressure baseline offset. The vent may be closed to set a static ear canal pressure or to generate ear canal pressure sweeps with an incidental baseline offset. The vent may be controlled to generate ear canal pressure sweeps with an intended baseline offset. The device produces ear canal pressure proportional to drive voltage, so any desired pressure versus time function can be generated by applying a coil driving voltage with the appropriate amplitude versus time function.

11 Claims, 5 Drawing Sheets

EAR CANAL PRESSURIZATION DEVICE

FIELD OF THE INVENTION

This invention generally relates to an ear canal pressurization device optimized for use during aural acoustic immittance testing. The disclosed device is a dual flexible chamber apparatus driven by a moving magnet linear motor. The device operates quietly and can generate a static ear canal pressure (below or above atmospheric) when driven by DC voltage or an alternating ear canal pressure function when driven by an AC voltage.

BACKGROUND OF THE INVENTION

The status of the middle ear system (tympanic membrane and ossicular chain) may be clinically ascertained by measuring aural acoustic immittance (AAI) at the entrance to the ear canal (immittance refers to either admittance or impedance). Typically, AAI measures are made as air pressure in the ear canal is parametrically varied below or above atmospheric pressure. AAI measures are obtained by sealing the tip of a probe, surrounded by a flexible cuff, in the opening to an ear canal, and the probe includes an air line through which pressure changes may be introduced. Ear canal pressure is monitored via a pressure transducer, and a control loop may be used to maintain or vary the pressure. Two commonly employed middle ear assessment tests based on AAI measures are tympanometry and acoustic reflex testing. In tympanometry, aural acoustic immittance is measured as air pressure in the ear canal is parametrically varied (e.g., +200 to −300 daPa) and a plot of immittance versus ear canal pressure during the pressure sweep is referred to as a tympanogram. The tympanogram provides a means to indirectly measure pressure in the middle ear cavity, since maximal admittance (or minimal impedance) occurs when ear canal pressure is equal to middle ear pressure. During acoustic reflex testing, ear canal pressure is maintained at the value that produced maximal admittance (minimal impedance) as inferred from the tympanogram, and changes in AAI are monitored as acoustic reflex eliciting stimuli are presented.

Thus, an ear canal pneumatic system suitable for AAI measurement requirements must be capable of providing an ear canal pressure sweep during tympanometric testing and of maintaining a static ear canal pressure during acoustic reflex testing. Noise produced by the pressure generation mechanism must be minimal, or the noise may be detected by the AAI measurement system and be misinterpreted as an admittance change, particularly during acoustic reflex testing. Ideally, an ear canal pressurization system should employ a reliable and easily implemented drive means and should yield a linear pressure versus drive function to ensure control loop stability. Lastly, an ideal ear canal pressurization system should have a long and maintenance-free life span.

AAI instrument pneumatic systems typically utilize syringe/plunger systems, oscillating diaphragm pumps, or peristaltic pumps. None of these systems meet all of the above stated requirements. Syringe/plunger systems are driven by stepper motors with rotary-to-linear gear drives. They require a stepper motor controller, acoustic damping in the air line to reduce stepper motor noise, and are prone to leakage due to plunger seal wear. Syringe/plunger systems also require valves to allow the plunger to be repositioned when plunger extents are reached before target pressure is achieved (e.g., in the presence of an air leak). Oscillating diaphragm pumps are flow-governed and can recover from a slight air leak, once the leak is sealed, without the need for "reset" valves, but they require considerable acoustic damping in the air line and separate pressure and vacuum pumps, connected via an airflow restrictor. Oscillating diaphragm pumps also require tuning, since they perform optimally at a specific drive frequency, and this necessitates a more complicated calibration procedure. Peristaltic ("squeezed tube") pumps utilize a stepper motor driven roller to produce air pressure by rolling over and compressing a flexible tube so that a small quantity of air is trapped and moved in one direction or the other. These pumps require acoustic damping in the air line and they also require periodic replacement of the tubing, which is constantly stressed by the roller providing the "squeeze". Additionally, peristaltic pumps are prone to leaks when the spring force which holds the roller against the flexible tubing fails to fully pinch off the tubing. U.S. Pat. App. No. 2006/0197412 discloses an ear canal pressurization pump driven by a piezo electric motor. Such a pump would be quiet, since drive oscillations occur at a frequency above the range of human hearing, but the disclosed pump requires controlled valves to produce bidirectional pressure changes. Another disadvantage of piezo electric motors is that they require high frequency, high voltage driving signals and relatively sophisticated controllers.

BRIEF SUMMARY OF THE INVENTION

A purpose of the preferred embodiments of the present invention is to provide an ear canal pressurization device optimized for use during aural acoustic immittance testing. The disclosed device is comprised of a rigid mounting framework which holds in position a forcer assembly, a motor assembly, a first chamber assembly, and a second chamber assembly. The assemblies are axially aligned within the mounting framework, with the forcer assembly and motor assembly centrally located and the chamber assemblies distally located. The forcer assembly is comprised of a hollow cylindrical ferromagnetic core, bounded by ferromagnetic washers and comprising a bobbin form on which is wound a length of magnet wire to form a coil. The motor assembly is comprised of a rigid chamber link fitted with a keeper washer and ring magnet at each end. The chamber link passes through, without touching, the hollow core of the forcer assembly. The first and second chamber assemblies are each comprised of flexible chambers mounted to rigid end plates. The first chamber assembly is situated at a first distal end of the mounting framework, and attached at its medial boundary to the first keeper washer of the motor assembly. The second chamber assembly is situated at a second distal end of the mounting framework, oriented in the opposite direction as the first chamber assembly, and attached at its medial boundary to the second keeper washer of the motor assembly. Current flow through the coil of the forcer assembly provides motive force re the Lorentz force equation (i.e., force equals flux density times current) for the moving magnet linear motor, and movement of the motor increases the volume of the first flexible chamber while decreasing the volume of the second flexible chamber, or vice versa. The first flexible chamber provides elastic suspension for a first end of the motor assembly, and the second flexible chamber provides symmetrical elastic suspension for a second end of the motor assembly. In the absence of current flow through the forcer coil, the motor assembly is elastically suspended, and centrally disposed, between the first chamber assembly and the second chamber assembly. The internal volume of the first flexible chamber is coupled to an ear canal via an air line so that changes in said internal volume produce changes in ear canal pressure re Boyle's law. The internal volume of the second flexible chamber is vented to ambient air pressure.

Static ear canal pressure is produced by moving the motor to adjust and maintain the volume of the first flexible chamber. An ear canal pressure sweep is produced by moving the motor to adjust the volume of the first flexible chamber to a first extent, and then adjusting the volume in the opposite direction to a second extent. An alternating ear canal pressure sweep is produced by periodically repeating a pressure sweep, but the alternating pressure function will likely have a baseline offset. Inclusion of a voltage controlled valve to open or close a small vent (e.g., a capillary tube) provides ability to control or to remove pressure baseline offset. The cross-sectional area of the vent is chosen to give a pressure discharge time constant of several seconds so that little pressure loss through the vent will occur for typical alternating pressure generation sweep rates. A symmetrical alternating ear canal pressure sweep without baseline offset can be produced by opening the vent with the motor at the rest position to equalize air pressure to ambient, adjusting the volume of the first flexible chamber to a first extent, adjusting the volume in the opposite direction to a second extent, adjusting the volume back to the first extent, and repeating. An alternating ear canal pressure sweep with an intended baseline offset (e.g., +200 to −300 daPa) can be produced using one of three methods. The first method is to drive the coil with a symmetrical AC waveform having a DC offset. The second method is accomplished by opening the vent, adjusting the first flexible chamber volume to a first extent to provide the DC offset, closing the vent, and driving the coil with a symmetrical AC waveform with no DC offset. The third method is accomplished by opening the vent and driving the coil with an asymmetrical AC wave form having no DC offset and lesser positive amplitude and greater negative amplitude. Those skilled in the art will appreciate that any number of pressure functions may be generated by varying the amplitude versus time function of the coil driving voltage.

A disclosed embodiment of the ear canal pressurization device can be driven by a DC voltage to provide a static ear canal pressure, and can be driven by an AC voltage to produce an alternating ear canal pressure function. The embodiment utilizes Boyle's gas law principle to vary ear canal air pressure by changing the volume of a flexible chamber coupled to an ear canal. The volume of said flexible chamber is varied via a moving magnet linear motor driven by a forcer in one direction to compress said flexible chamber, which decreases its internal volume to increase pressure, or in the opposite direction to expand said flexible chamber, which increases its internal volume to decrease pressure. The device operates quietly to avoid interference with AAI measurement, and should have a long and maintenance free life span.

In a preferred embodiment of the ear canal pressurization device, the enclosed volume of the first flexible chamber is coupled, via an air line, to the ear canal, to a pressure transducer, and through a controlled valve to a small air vent (e.g., a capillary tube). The valve is closed to allow setting a static pressure, controlled to generate an alternating pressure sweep with a baseline offset, or opened to generate an alternating pressure sweep with no baseline offset or to allow ear canal pressure to equalize to ambient pressure.

In another embodiment of the invention, the ear canal pressurization device is utilized with or without venting, but with no valve. This embodiment would be less expensive to implement, would obviate the need for valve control, and would be suitable for tympanometric screening tests.

In other embodiments of the invention, the mounting scheme for the first chamber assembly, forcer assembly, motor assembly, and second chamber assembly may be modified in various ways. For example, the assemblies could be mounted within an arrangement of three cylindrical tubes, so that the length of each tube determines the spacing between assemblies. Other mounting arrangements are also possible, as long as proper spacing is maintained among the assemblies.

In other embodiments of the invention, the shape or size of the chamber assemblies, forcer assembly, and motor assembly could be adapted to facilitate inclusion of the device in a particular cabinet or other container as long as the elastic characteristics of the flexible chambers and the electromagnetic characteristics of the forcer and motor assemblies fall within the parameters required for proper device function. The basic premise of the design could also be extended by adding additional flexible chambers and motor assemblies to provide multiple pressure generation point sources.

In another embodiment of the invention, the internal volume of the first flexible chamber could be coupled, with or without a valved vent, to a first air line and the internal volume of the second flexible chamber could be coupled, with or without a valved vent, to a second air line, so that movement of the motor assembly in a first direction would simultaneously produce a pressure increase in the first air line and a pressure decrease in the second air line.

This disclosure discloses a device for parametrically varying air pressure in an ear canal, said device comprising: a first chamber assembly including a first flexible chamber attached, and hermetically sealed, to a first supporting end plate structure, said first flexible chamber enclosing a volume of air which is coupled, via an air line from an air line fitting in said first supporting end plate structure, to an ear canal; a second chamber assembly including a second flexible chamber attached to a second supporting end plate structure, said second flexible chamber enclosing a volume of air coupled via an opening in said second end plate structure to ambient air pressure; a motor assembly including a rigid non ferromagnetic chamber link, said chamber link being fitted on a first end with a first ferromagnetic keeper washer and first rare earth ring magnet, said chamber link being fitted on a second end with a second ferromagnetic keeper washer and second rare earth ring magnet, said first and second ring magnets oriented with like poles facing each other whereby the first flexible chamber can be compressed and the second flexible chamber can be expanded, or vice versa, by application of an electromagnetic field which attracts the first ring magnet and repels the second ring magnet, or vice versa; and a forcer assembly, disposed equidistant between the first chamber assembly and the second chamber assembly, said forcer assembly comprising a bobbin formed of a hollow cylindrical ferromagnetic core bounded at either end by ferromagnetic washers, said ferromagnetic core wound with a length of magnet wire to form a coil, said coil providing an electromagnetic field for moving the motor assembly when current flows through said coil, wherein the device is configured in accordance with the requirements of aural acoustic immittance testing. The device may further include a controlled valve attached along the air line to couple the air line through a small vent to ambient pressure, the size of said vent being chosen to give a pressure discharge time constant of several seconds so that pressure loss through the vent is minimal for typical alternating pressure generation sweep rates.

This disclosure further discloses a method for producing a pressure change in an ear canal using the device described above, the method comprising the step of applying a DC or AC driving voltage to the coil of the forcer assembly, said voltage resulting in movement of the motor assembly to change the volume of the air space enclosed by the first flexible chamber, said change in volume resulting in a proportional change in ear canal pressure according to Boyle's gas law. The method may further include the steps of: producing changes in ear canal pressure proportional to the driving voltage; and selecting a magnetic flux density of the first ring magnet and the second ring magnet, respectively, to achieve a balance between a motor assembly drive force provided by the forcer assembly, and an elastic restorative force of the first and second flexible chambers when the motor is axially displaced from its rest position, said balance between the motor assembly drive force and the elastic restorative force resulting in a substantially linear relationship between actual motor displacement and driving voltage.

This disclosure also discloses a method for producing a pressure change in an ear canal using the device of claim 4, the method comprising the steps of: applying a DC or AC driving voltage to the coil of the forcer assembly, said voltage resulting in movement of the motor assembly to change the volume of the air space enclosed by the first flexible chamber, said change in volume resulting in a proportional change in ear canal pressure according to Boyle's gas law; producing changes in ear canal pressure proportional to the driving voltage; and selecting a magnetic flux density of the first ring magnet and the second ring magnet, respectively, to achieve a balance between a motor assembly drive force provided by the forcer assembly, and an elastic restorative force of the first and second flexible chambers when the motor is axially displaced from its rest position, said balance between the motor assembly drive force and the elastic restorative force resulting in a substantially linear relationship between actual motor displacement and driving voltage.

The method may further include the step of opening the vent valve to allow a graded recovery of ear canal pressure to ambient air pressure in the absence of drive voltage to the coil.

Additionally or alternatively, the method may further include the steps of: opening the valve; and driving the coil with an alternating voltage, said alternating voltage having equal positive and negative peak amplitudes, to produce a symmetrical alternating ear canal pressure function free of baseline offset.

Additionally or alternatively, the method may further include the steps of: opening the valve to allow ear canal pressure to equalize to ambient pressure; closing the valve; driving the coil with an alternating voltage, said alternating voltage having a DC offset, and said alternating voltage having equal positive and negative peak amplitudes, thereby producing a symmetrical alternating ear canal pressure function with an intended baseline offset.

Additionally or alternatively, the method may further include the steps of: opening the valve to allow ear canal pressure to equalize to ambient pressure; closing the valve; shifting the motor to a first position to provide a pressure baseline offset; and driving the coil with an alternating voltage, said alternating voltage having no DC offset, and said alternating voltage having equal positive and negative peak amplitudes, thereby-producing a symmetrical alternating ear canal pressure function with an intended pressure baseline offset.

Additionally or alternatively, the method may further include the steps of: opening the valve; and driving the coil with an alternating voltage, said alternating voltage having no DC offset, and said alternating voltage having lesser positive and greater negative peak amplitudes, or vice versa, thereby producing an asymmetrical alternating ear canal pressure function free of baseline offset.

Additionally or alternatively, the method may further include a method wherein the producing step further comprises creating a negative pressure in a patient's ear during one or more time periods while alternating pressure generation sweeps are taking place.

In summary, this disclosure provides several advantages for the implementation of an ear canal pneumatic system suitable for use during AAI testing. The device operates quietly, which minimizes the need for acoustical damping in the air line. The device requires only a DC or AC driving voltage in place of a more complicated drive means (e.g., stepper motor control and gear drive). The device produces pressure changes by increasing or decreasing the volume of a flexible chamber, and may be used to set static ear canal pressure or to generate a variety of ear canal pressure functions. The ear canal pressurization device is relatively simple to implement and should have a virtually unlimited and maintenance free life span, determined primarily by the properties of the material used for the first and second flexible chambers.

While some embodiments have been described above, the embodiments are exemplary, not limiting, and it should be readily understood that such embodiments of the invention are susceptible to a variety of modifications and configurations. Therefore, having summarized various aspects of the embodiments of the invention in simplified form, some embodiments will now be described in greater detail with reference to the following figures wherein similar reference numerals designate similar features throughout the figures.

DETAILED DESCRIPTION OF THE INVENTION

Figure 1:
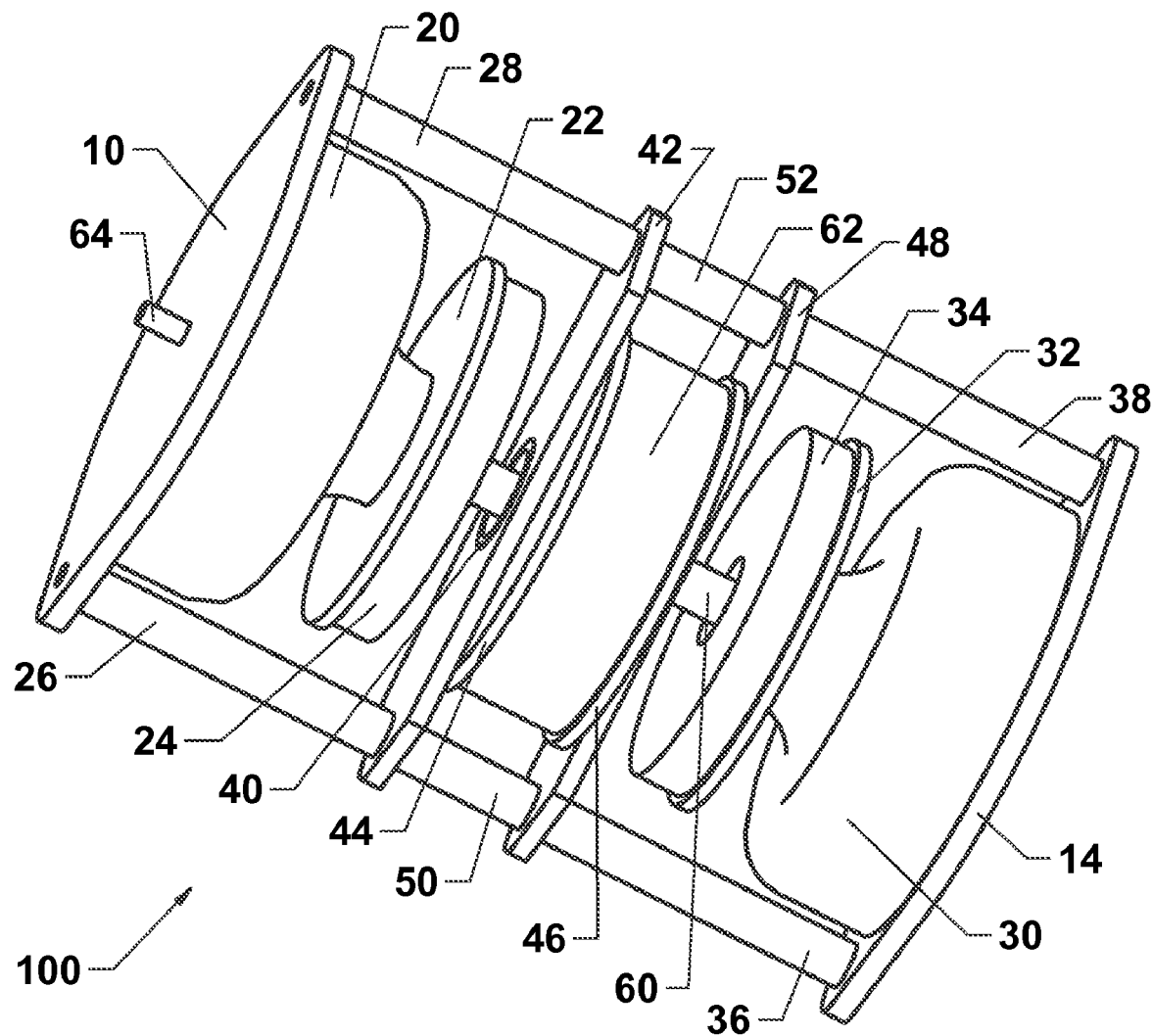
FIG. 1 shows a perspective view of an embodiment of the ear canal pressurization device according to the present invention.
Figure 2:
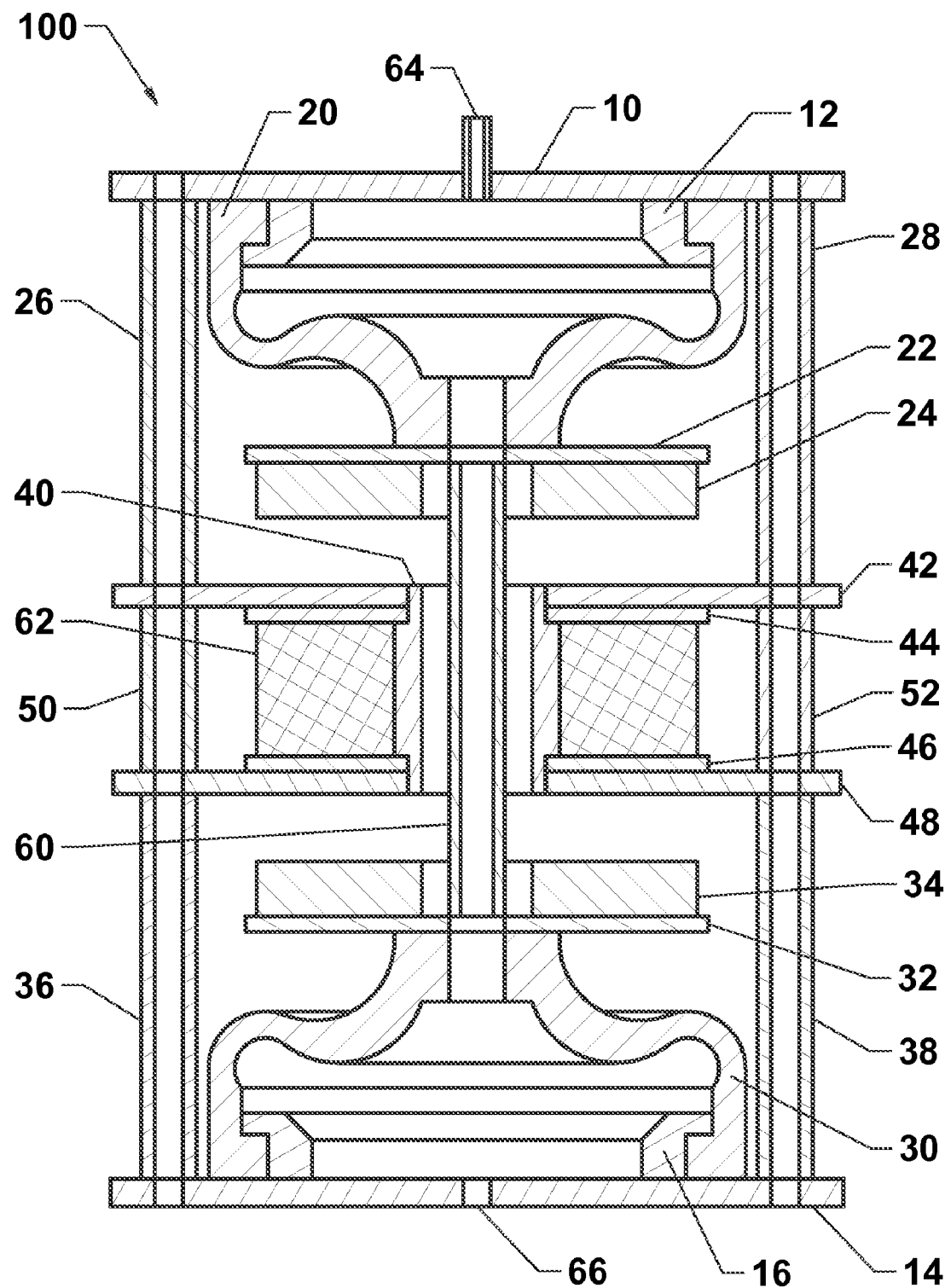
FIG. 2 shows a sectional view of an embodiment of the ear canal pressurization device according to the present invention.
Figure 6:
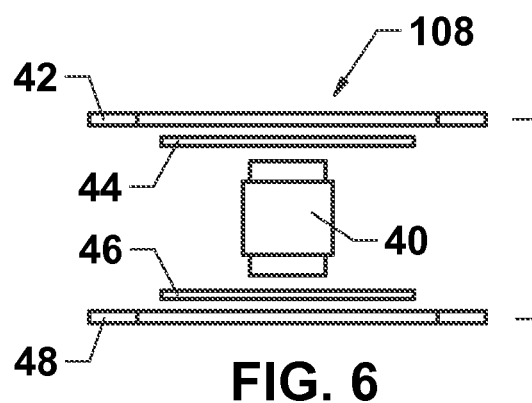
FIG. 6 shows an exploded view of an embodiment of the forcer assembly, with coil omitted, of the ear canal pressurization device according to the present invention.

A preferred embodiment of an ear canal pressurization device 100 is shown in FIGS. 1, 2, and 6.

The forcer assembly 108 includes a first forcer assembly mounting bracket 42, a first forcer assembly washer 44, a forcer assembly core 40, a second forcer assembly washer 46, and a second forcer assembly mounting bracket 48. Said first and second forcer assembly mounting brackets are preferably made of non-ferromagnetic material (e.g., plastic or aluminum) and, along with forcer assembly spacers 50 and 52, provide mounting for the forcer assembly. The forcer assembly core 40 preferably includes a rigid length of cylindrical, hollow, ferromagnetic material (e.g., iron) with inner diameter sufficiently large to allow a chamber link 60 to pass through without touching the forcer assembly core 40. Said forcer assembly core has a reduced diameter at one end to receive the first forcer assembly washer 44 and first forcer assembly mounting bracket 42, which are press fit onto a first end of the forcer assembly core 40, and a reduced diameter at the opposite end to receive the second forcer assembly washer 46 and second forcer assembly mounting bracket 48, which are press fit onto a second end of the forcer assembly core 40. Thickness of the first forcer assembly mounting bracket 42 is chosen sufficient to prevent magnetic "lockup" between a first ring magnet 24 and ferromagnetic first forcer assembly washer 44, and thickness of the second forcer assembly mounting bracket 48 is chosen sufficient to prevent magnetic "lockup" between a second ring magnet 34 and ferromagnetic second forcer assembly washer 46. The first forcer assembly washer 44 and second forcer assembly washer 46 includes the distal retaining walls, and forcer assembly core 40 includes the base, of a bobbin form around which is wrapped a length of insulated magnet wire to form a coil 62; said coil providing an electromagnetic field when current flows through said coil. The ferromagnetic forcer assembly washers, 44 and 46, serve to intensify and axially align the electromagnetic field generated at distal ends of the forcer assembly core 40 and also provide increasing attractive electromagnetic forces which act to balance the increasing flexible chamber elastic forces as the first or second ring magnet, 24 or 34, respectively, approaches the forcer assembly 108.

Figure 4:
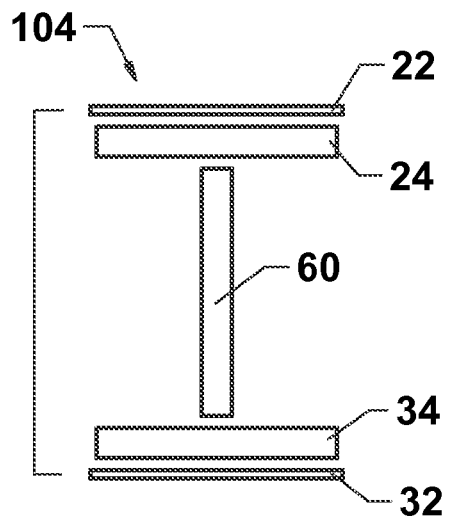
FIG. 4 shows an exploded view of an embodiment of the motor assembly of the ear canal pressurization device according to the present invention.

A motor assembly 104 is shown in FIG. 4 and includes first keeper washer 22, the first ring magnet 24, the chamber link 60, the second ring magnet 34 and a second keeper washer 32. The first and second keeper washers, 22 and 32, respectively, are each preferably made of ferromagnetic metal. The first ring magnet 24, preferably made of a rare earth (e.g., neodymium) magnetic material, axially magnetized, is centered on and attached (e.g., via suitable glue) to the medial margin of the first keeper washer 22. Said first ring magnet 34 is oriented so that either pole (e.g., north) faces medially. The second ring magnet 34, identical to the first ring magnet 24, is centered on and attached (e.g., via suitable glue) to the medial margin of the second keeper washer 32. Said second ring magnet is oriented with the same pole facing medially as selected for the first ring magnet 24; i.e., like magnetic poles face each other. Those skilled in the art will appreciate that first and second ring magnets, 24 and 34, respectively, will provide the same function if both are reversed in polarity. The diameters of the first and second keeper washers, 22 and 32, respectively, are chosen sufficiently larger than the diameters of the first and second ring magnets, 24 and 34, respectively, to ensure that said first and second ring magnets tend to auto-center on said first and second keeper washers, respectively, and that the magnetic flux fields of said first and second ring magnets are concentrated through said first and second keeper washers, respectively. The chamber link 60 preferably includes a rigid non ferromagnetic coupling between the first keeper washer 22 and the second keeper washer 32. The first keeper washer 22 is attached, via suitable means, on its medial margin to a first end of the chamber link and on its distal margin to the medial margin of the first flexible chamber 20. The second keeper washer 32, is attached, via suitable means on its medial margin to a second end of the chamber link 60 and on its distal margin to the medial margin of the second flexible chamber 30. The chamber link 60 passes through, without touching, the cylindrical opening in the forcer assembly core 40. Length of said chamber link is chosen with respect to lengths of the chamber assembly spacers (26, 28, 36, and 38), secured in position via suitable mechanical means, and lengths of the forcer assembly spacers (50 and 52), secured in position via suitable mechanical means, so that the motor assembly 104 is elastically suspended between the first flexible chamber 20 and the second flexible chamber 30 when a first chamber assembly 102, the motor assembly 104, and a second chamber assembly 106 are held in place by said chamber assembly spacers and said forcer assembly spacers.

Figure 3:
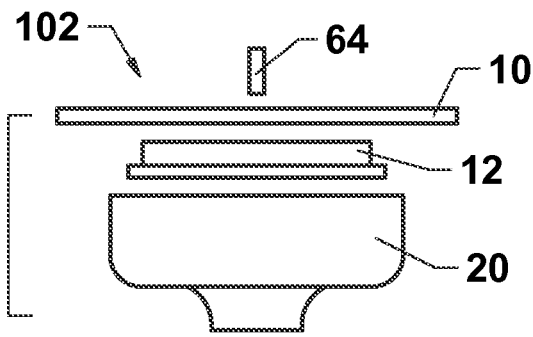
FIG. 3 shows an exploded view of an embodiment of the first chamber assembly of the ear canal pressurization device according to the present invention.

The first chamber assembly 102 (FIG. 3) includes a first end plate 10, a first retaining ring 12, a first flexible chamber 20, and an air line fitting attachment 64. The first end plate 10 includes a flat, rigid plate which provides attachment points near an outer extent for chamber assembly spacers 26 and 28, and incorporates, via a hole drilled in said first end plate, the air line attachment fitting 64 (e.g., simple tube or commercial air line fitting) used to couple the internal volume of the first flexible chamber 20 to an air line 70. The first retaining ring 12 is centered on and attached to, via suitable means, the medial margin of the first end plate 10. The first flexible chamber 20 includes a suitably elastic material (e.g., rubber), with dimensions chosen to provide a volume of enclosed air suitable for producing the needed range of ear canal pressure changes re Boyle's law for the available range of motor assembly 104 movement, and shape of the medial end chosen to provide essentially plunger-like movement of said medial end. The distal end of the first flexible chamber 20 fits over the first retaining ring 12, the distal end of said first flexible chamber being sufficiently flexible to be stretched over said first retaining ring, and to subsequently recover its shape so that an air tight fit of said first flexible chamber over said first retaining ring may be achieved via the application of a minimal amount of viscous sealant (e.g., grease) between said first retaining ring and said first flexible chamber.

Figure 5:
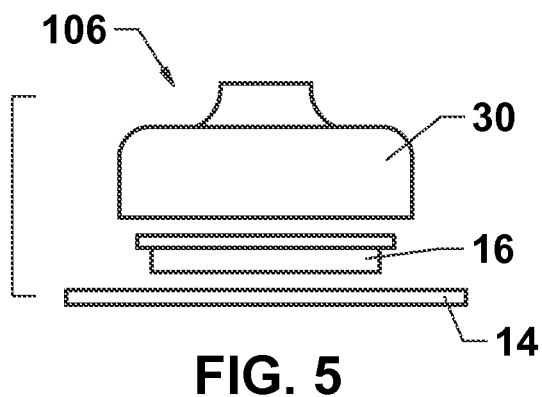
FIG. 5 shows an exploded view of an embodiment of the second chamber assembly of the ear canal pressurization device according to the present invention.

The second chamber assembly 106 (FIG. 5) includes a second end plate 14, a second retaining ring 16, and a second flexible chamber 30. The second end plate 14 includes a flat, rigid plate which provides attachment points near an outer extent for chamber assembly spacers 36 and 38, and incorporates an opening (e.g., a small hole) that couples the internal volume of the second flexible chamber 30 to ambient air pressure. The second retaining ring 16 is centered on and attached, via suitable means, to the medial margin of the second end plate 14. The second flexible chamber 30 is preferably identical within manufacturing tolerances to the first flexible chamber 20. The distal end of the second flexible chamber 30 fits over the second retaining ring 16, the distal end of said second flexible chamber being sufficiently flexible to be stretched over said second retaining ring, and to subsequently recover its shape. Hermetic seal of the second flexible chamber 30 to the second end plate 14 is not required; the function of the second flexible chamber 30 is to provide symmetrical elastic suspension and increased elastic restorative force for the motor assembly 104.

When current flows through the coil 62, a magnetic field is generated, said magnetic field lines of force being orthogonal to the direction of the current flow. The first ring magnet 24 and the second ring magnet 34 are axially magnetized and oriented with like poles facing medially (i.e., like poles facing each other). Axial magnetization of the first and second ring magnets, 24 and 34, respectively, ensures that the electromagnetic force produced by current flow through the coil 62 is primarily directed along the movement axis of the motor 104, and radial forces, which would move said motor off-axis are nearly eliminated. Current flow through the coil 62 in a first direction repels the first ring magnet 24 and attracts the second ring magnet 34, and the motor assembly 104 moves in a first direction. Current flow through the coil 62 in the opposite direction attracts the first ring magnetic 24 and repels the second ring magnet 34 and the motor assembly 104 moves in a second direction.

Figure 7:
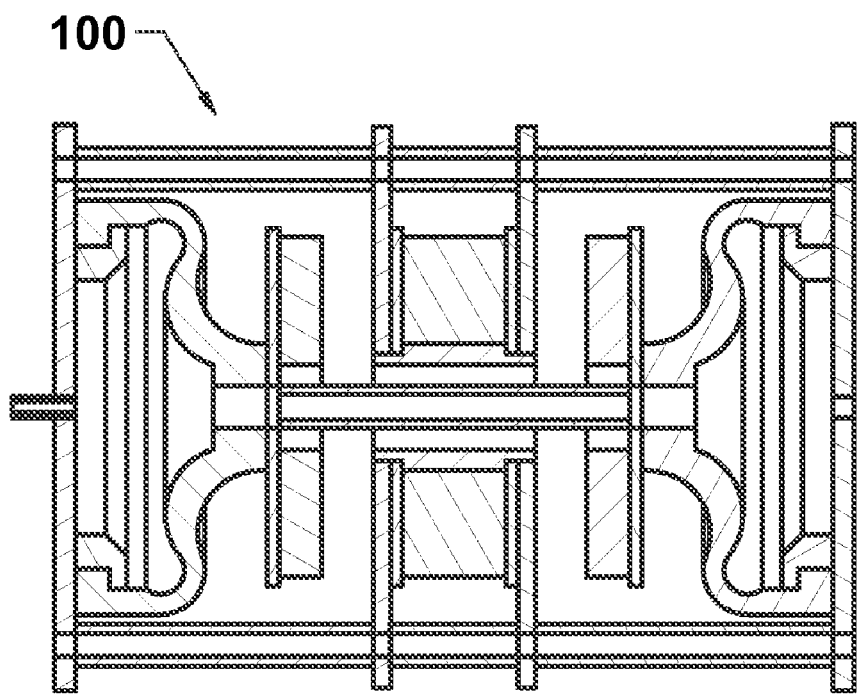
FIG. 7 shows a sectional view of an embodiment of the ear canal pressurization device with the motor in the centered (rest) position.
Figure 8:
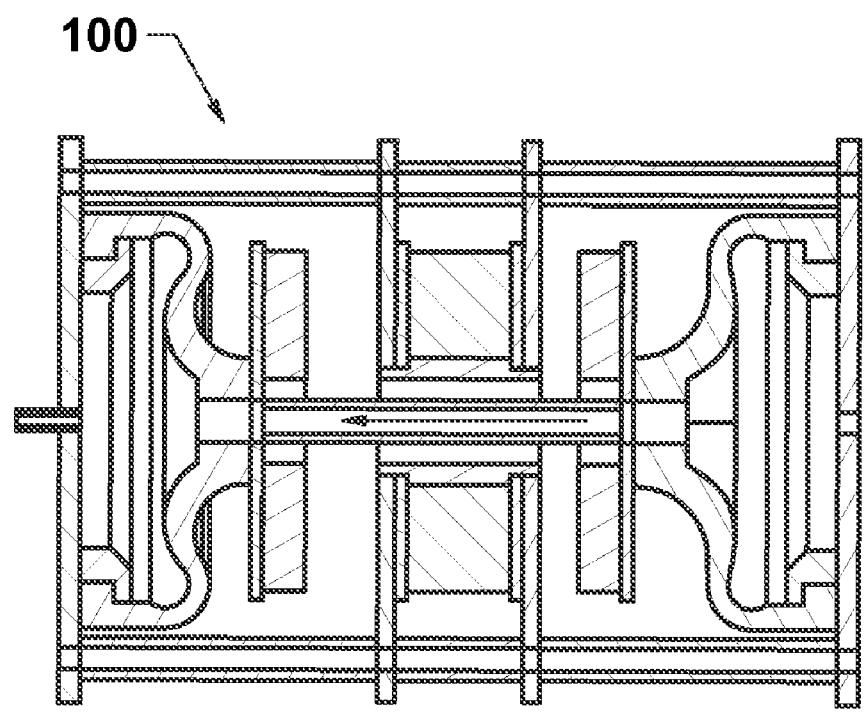
FIG. 8 shows a sectional view of an embodiment of the ear canal pressurization device in which the motor has been displaced in a first direction.

The elastic characteristics of the first and second flexible chambers, 20 and 30, respectively, the method used for suspension of the motor assembly 104, and electromagnetic characteristics of the forcer assembly 108 are chosen to ensure that ear canal pressure generation is proportional to drive voltage. In the rest state (i.e., when there is no drive voltage to the coil 62), the motor assembly 104 is elastically suspended so that said motor assembly self centers between the first and second flexible chambers, 20 and 30, respectively (FIG. 7). When a driving voltage is applied to the coil 62 with a first polarity, the motor assembly 104 moves in a first direction, and the first flexible chamber 20 is compressed as the second flexible chamber 30 is elongated (FIG. 8). Motor assembly 104 movement in the first direction is primarily due to the attractive force between the second ring magnet 34 and the forcer assembly 108, since this force increases in accordance with the inverse square law, while the repellant force between the first ring magnet 24 and the forcer assembly 108 decreases in accordance with the inverse square law. As the second ring magnet 34 moves closer to the forcer assembly 108, the inverse square law attraction tends to counteract the combined elastic restorative force created by compression of the first flexible chamber 20 and elongation of the second flexible chamber 30. When a driving voltage is applied to the coil 62 with a second polarity, opposite to the first polarity, the motor assembly 104 moves in a second direction, and the first flexible chamber 20 is elongated as the second flexible chamber 30 is compressed. Motor assembly 104 movement in the second direction is primarily due to the attractive force between the first ring magnet 24 and the forcer assembly 108, since this force increases in accordance with the inverse square law, while the repellant force between the second ring magnet 34 and the forcer assembly 108 decreases in accordance with the inverse square law. As the first ring magnet 24 moves closer to the forcer assembly 108, the inverse square law attraction tends to counteract the elastic restorative force created by the elongation of the first flexible chamber 20 and the compression of the second flexible chamber 30. The proper balance between the electromotive force (i.e., the force imparted by the forcer assembly 108 on the motor assembly 104) and the elastic restorative force is established by selecting first and second ring magnets, 24 and 34, respectively, with an appropriate flux density, and by winding the coil 62 to provide an appropriate electromotive force.

Compression of the first flexible chamber 20 results in a decreased volume within the chamber and elongation of the first flexible chamber 20 results in an increased volume within the chamber. Changes in volume of the first flexible chamber 20, attached via an air line 70 to an ear canal 92, result in changes in ear canal pressure re Boyle's Law; i.e., pressure increases in proportion to a decrease in volume, and vice versa. The pressure/time function generated within the ear canal 92 will be proportional to the amplitude/time function of the driving voltage applied to the coil 62 when balance is achieved among the elastic restorative forces of the first and second flexible chambers, 20 and 30, respectively, the magnetic flux density of the first and second ring magnets, 24 and 34, respectively, and the electromotive motor provided by current flow through the coil 62 over the required range of motor assembly 104 movement.

Figure 9:
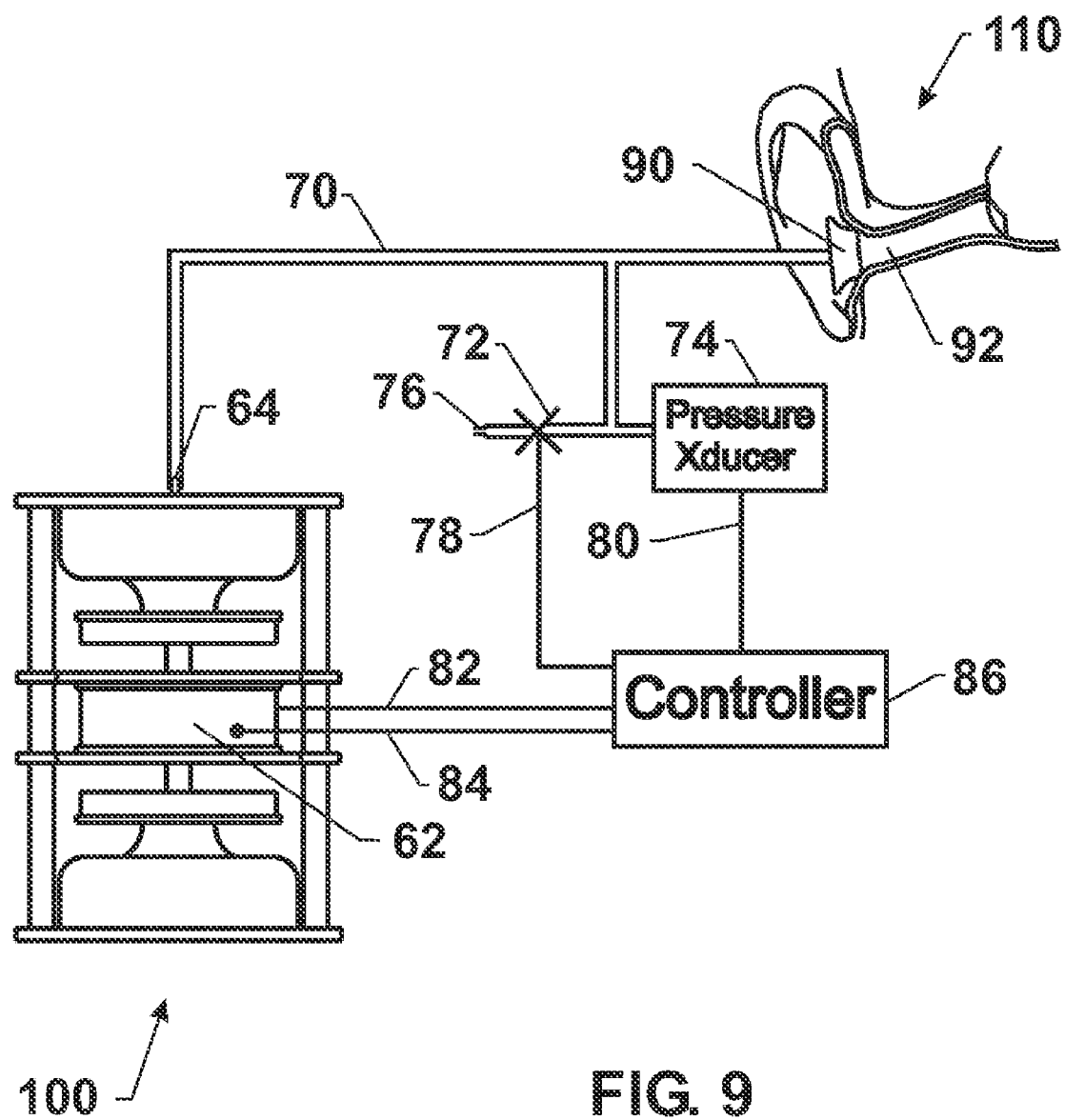
FIG. 9 shows a block diagram of a typical application of the ear canal pressurization device 100.

FIG. 9 shows a block diagram of a typical implementation of a disclosed embodiment to produce pressure changes in the ear canal 92 of a human ear 110. An air line 70 is attached to the air line fitting 64 of the ear canal pressurization device 100. Said air line is routed to a flexible cuff 90 that is sealed in the opening to an ear canal 92, to a pressure transducer 74, and through a valve 72 to a small air vent 76. A controller 86 (e.g., a microcontroller or a digital signal processor) monitors an air pressure signal 80 from the pressure transducer 74, provides a valve control line 78 for operating the valve 72, provides a bi-directional DC or AC driving voltage to coil 62 via connecting wires 82 and 84, and implements an analog or digital automatic pressure control with pressure transducer reading (i.e., air pressure signal 80) as input and coil driving voltage (i.e., voltage on wires 82 and 84) as output. A number of different pressure functions may be generated using this basic implementation. To generate a static ear canal pressure, the controller 86 closes the valve 72 and adjusts the drive voltage to the coil 62 until the pressure transducer signal 80 indicates that the target ear canal pressure has been achieved. To generate an ear canal pressure sweep, the controller 86 opens the valve 72 to equalize ear canal pressure to ambient air pressure, closes said valve, adjusts coil 62 driving voltage to achieve a first target pressure, indicated by signal 80, and adjusts coil 62 driving voltage in an opposite polarity to achieve a second target pressure, indicated by signal 80. An alternating ear canal pressure function may be generated by periodically repeating an ear canal pressure sweep with the valve 72 closed if a small baseline offset (e.g., due to probe placement or a transient, unintended, air leak) is acceptable. An alternating pressure sweep free of baseline offset may be generated by leaving the valve 72 open and driving the coil 62 with a symmetrical AC voltage. An alternating pressure function with asymmetrical positive and negative peak amplitudes such as +200 to −300 daPa may be generated by applying a coil 62 driving voltage which contains a DC offset, or by opening the valve 72, moving the motor assembly 104 to a preset position to provide the pressure baseline offset, then closing the valve 72 and driving the coil 62 with a voltage having symmetrical positive and negative peak amplitudes, or by opening the valve 72 to equalize ear canal pressure to ambient air pressure, then closing the valve and driving the coil 62 with a voltage having asymmetrical positive and negative peak amplitudes (e.g., greater negative peak amplitude and lesser positive peak amplitude). Those skilled in the art will appreciate that any number of pressure versus time functions may be generated by varying the amplitude versus time function of the drive voltage to the coil 62.

In view of the above explanation of the particular features of the present invention, one skilled in the art will readily appreciate that the present invention can be used to generate the ear canal pressure functions required for aural acoustic immittance testing, and that the device can be usefully employed in a wide variety of embodiments. While certain embodiments and implementations have been disclosed and discussed above, the embodiments and implementations are intended to be exemplary only and not limiting of the present invention. The appropriate scope of the invention is defined by the claims set forth below.

What is claimed is:

1. A device for parametrically varying air pressure in an ear canal in accordance with the requirements of aural acoustic immittance testing, said device comprising:

a first chamber assembly including a first flexible chamber attached, and hermetically sealed, to a first supposing end plate structure, said first flexible chamber enclosing a volume of air which is coupled, via an air line from an air line fitting in said first supporting end plate structure, to an ear canal;

a second chamber assembly including a second flexible chamber attached to a second supporting end plate structure, said second flexible chamber enclosing a volume of air coupled via an opening in said second end plate structure to ambient air pressure;

a motor assembly including a rigid non ferromagnetic chamber link, said chamber link being fitted on a first end with a first ferromagnetic keeper washer and first rare earth ring magnet, said chamber link being fitted on a second end with a second ferromagnetic keeper washer and second rare earth ring magnet, said first and second ring magnets with like poles magnetically opposing each other whereby the first flexible chamber can be compressed and the second flexible chamber can be expanded, or vice versa, by application of an electromagnetic field which attracts the first ring magnet and repels the second ring magnet, or vice versa; and a forcer assembly, disposed equidistant between the first chamber assembly and the second chamber assembly, said forcer assembly comprising a bobbin formed of a hollow cylindrical ferromagnetic core bounded at either end by ferromagnetic washers, said ferromagnetic core wound with a length of magnet wire to form a coil, said coil providing an electromagnetic field for moving the motor assembly when current flows through said coil.

2. The device of claim 1 further comprising a controlled valve attached along the air line to couple the air line through a small vent to ambient pressure, the size of said vent being chosen to give a pressure discharge time constant of several seconds so that pressure loss through the vent is minimal for typical alternating pressure generation sweep rates.

3. A method for producing a pressure change in an ear canal using the
device of claim 1, the method comprising the step of applying a DC or AC driving voltage to the coil of the forcer assembly, said voltage resulting in movement of the motor assembly to change the volume of the air space enclosed by the first flexible chamber, said change in volume resulting in a proportional change in ear canal pressure according to Boyle's gas law.

4. The method of claim 3 further comprising the steps of:
producing changes in ear canal pressure proportional to the driving voltage;
selecting a magnetic flux density of the first ring magnet and the second ring magnet, respectively, to achieve a balance between a motor assembly drive force provided by the forcer assembly, and an elastic restorative force of the first and second flexible chambers. when the motor is axially displaced from its rest position, said balance between the motor assembly drive force and the elastic restorative force resulting in a substantially linear relationship between actual motor displacement and driving voltage.

5. A method for producing a pressure change in an ear canal using the device of claim 2, the method comprising the steps of:
applying a DC or AC driving voltage to the coil of the forcer assembly, said voltage resulting in movement of the motor assembly to change the volume of the air space enclosed by the first flexible chamber, said change in volume resulting in a proportional change in ear canal pressure according to Boyle's gas law;

producing changes in ear canal pressure proportional to the driving voltage; and selecting a magnetic flux density of the first ring magnet and the second ring magnet, respectively, to achieve a balance between a motor assembly drive force provided by the forcer assembly, and an elastic restorative force of the first and second flexible chambers when the motor is axially displaced from its rest position, said balance between the motor assembly drive force and the elastic restorative force resulting in a substantially linear relationship between actual motor displacement and driving voltage.

6. The method of claim 5 further comprising the step of opening the vent valve to allow a graded recovery of ear canal pressure to ambient air pressure in the absence of drive voltage to the coil.

7. The method. of claim 5 further comprising the steps of:
opening the valve; and
driving the coil with an alternating voltage, said alternating voltage having equal positive and negative peak. amplitudes. To produce a Symmetrical alternating ear canal pressure function free of baseline offset.

8. The method of claim 5 further comprising the Steps of:
opening the
valve to allow ear canal pressure to equalize to ambient pressure;
closing the valve;
driving the coil with, an alternating voltage, said alternating voltage having a DC offset, and said alternating voltage having equal, positive and negative peak amplitudes, thereby producing, a symmetrical alternating ear canal pressure function with an intended baseline offset.

9. The method of claim 5 further comprising the steps of:
opening the valve to allow ear canal pressure to equalize to ambient pressure;
closing the valve;
shifting the motor to a first position to provide a pressure baseline offset; and
driving the coil with an alternating Voltage, said alternating voltage having no DC offset, and said alternating voltage having equal positive and negative peak amplitudes, thereby-producing a symmetrical alternating ear canal pressure function with an intended pressure baseline offset.

10. The method of claim 5 further comprising the steps of:
opening the valve; and
driving the coil with an alternating voltage, said alternating voltage having no DC offset, and said alternating voltage having lesser positive and greater negative peak amplitudes, or vice versa, thereby producing an asymmetrical alternating ear canal pressure function free of baseline offset.

11. The method of claim 5 Wherein the producing step further comprises creating a negative pressure in a patient's ear during one or more time periods while alternating pressure generation sweeps are taking place.

* * * * *